United States Patent
Denyer et al.

(12) 
(10) Patent No.: US 6,367,470 B1
(45) Date of Patent: Apr. 9, 2002

(54) NEBULISERS

(75) Inventors: Jonathan Stanley Harold Denyer, Chichester; Anthony Dyche, Hayling Island; Ivan Richard Prince, Hedge Edge, all of (GB)

(73) Assignee: Medic-Aid Limited (GB)

( * ) Notice: Subject to any disclaimer, the term of this patent is extended or adjusted under 35 U.S.C. 154(b) by 0 days.

(21) Appl. No.: 09/223,824

(22) Filed: Jan. 4, 1999

(30) Foreign Application Priority Data

Nov. 17, 1998 (GB) ............................................. 9823434

(51) Int. Cl.⁷ ............................................. A61M 11/00
(52) U.S. Cl. ............................. 128/200.14; 128/200.24; 128/203.12; 128/203.25
(58) Field of Search ............... 128/898, 200.14–200.24, 128/203.12–204.14, 204.18

(56) References Cited

U.S. PATENT DOCUMENTS

| | | |
|---|---|---|
| 3,741,208 A | 6/1973 | Jonsson |
| 4,533,082 A | 8/1985 | Maehara et al. ............ 239/102 |
| 4,819,629 A | 4/1989 | Jonson |
| 4,832,012 A * | 5/1989 | Raabe et al. ............ 128/200.21 |
| 5,261,601 A | 11/1993 | Ross et al. ............... 239/102.2 |
| 5,549,106 A | 8/1996 | Gruenke et al. |
| 5,584,468 A | 12/1996 | Meglino et al. |
| 5,694,920 A | 12/1997 | Abrams et al. |
| 5,823,179 A * | 10/1998 | Grychowski et al. .. 128/200.18 |
| 6,116,233 A * | 9/2000 | Denyer et al. ......... 128/200.18 |

FOREIGN PATENT DOCUMENTS

| | | |
|---|---|---|
| EP | 0 667 168 | 2/1994 |
| EP | 9627266 A2 | 12/1994 |
| GB | 2 077 444 | 6/1981 |
| GB | 2 294 402 | 10/1995 |
| GB | 2294402 | 5/1996 |
| WO | WO94/07607 | 4/1994 |
| WO | WO96/13292 | 5/1996 |
| WO | WO97/29851 | 8/1997 |
| WO | WO97/48431 | 12/1997 |

OTHER PUBLICATIONS

ISAM Focus Symposium: Aerosol Therapy with Small Volume Nebulizers: Laboratory To Bedside; "Breathing Patterns In Adult Patients", Sep. 4–5, 1996, Tours, France.

* cited by examiner

Primary Examiner—Glenn K. Dawson
(74) Attorney, Agent, or Firm—William A. Simons; Wiggin & Dana

(57) ABSTRACT

A nebuliser having elements for determining the duration of a pulse of atomisation during inspiration, including elements for measuring the tidal volume of a patient timing elements for measuring the duration of inspiration, elements for storing estimates of the volume of a patient's upper airway, and elements for calculating the duration of the pulse. The duration of the pulse is calculated on the basis of the tidal volume measured by the tidal volume measuring elements; the duration of inspiration measured by the timing elements, and the stored estimated volume of patient's upper airway from the storage elements.

13 Claims, 9 Drawing Sheets

Pulse time = 50% sum $\frac{(T1 + T2 + T3)}{3}$

Dose = Sum (P1 + P2 + ....)

PRIOR ART  Fig.3.

NEBULISERS

BACKGROUND OF THE INVENTION

1. Field of the Invention

This invention relates to nebulisers.

2. Brief Description of Art

Many different types of nebulisers are known for delivering medication directly into the lungs of a patient, usually for treatment of respiratory diseases. Nebulisers normally deliver medication in the form of droplets or a dry powder. In most nebulisers, atomisation of the medicament into a stream of air occurs continuously, regardless of whether the patient is inspiring or expiring. However, the effect of continuous atomisation is that a significant proportion of medication is lost during expiration.

Commonly known nebulisers are either pneumatically operated from a compressed air source connected to the nebuliser which atomises the liquid, or are ultrasonic nebulisers which use a piezo-electric crystal to atomise the liquid. More recently, a mesh-type nebuliser has been developed in which the medication is forced through a fine mesh in order to create droplets of the medication. The optimum diameter of medication particles or droplets is about 1–5 microns. If the particles or droplets are bigger than this, they are likely to be impacted in the airway before they reach the lungs, but if they are smaller than one micron, they tend to be carried out of the lungs again on exhalation without sedimenting in the lungs.

One known nebuliser analyses the pressure changes within the device during the first three breaths to determine an average shape of the breathing pattern. A timed pulse of atomisation is commenced upon start of subsequent inspirations such that atomisation occurs for the first 50% of the inspiration. This is illustrated in FIG. 1 where the breathing pattern and pulse are superimposed. This is effective in reducing the loss of medication during exhalation to about 3%. FIG. 1 shows the breaths in a graph of flow rate against time. When the treatment is commenced, a patient breathes in and out three times through the nebuliser before treatment commences. The first three breaths are measured so that the timed pulse of atomisation occurs for 50% of the average time of inhalation. The duration of inhalation is indicated as T1, T2 and T3. These timed periods are averaged, and divided by two in order to determine the pulse length for the next fourth breath where treatment starts. For each subsequent breath, the duration of the pulse of atomisation is determined by summing the time period of inhalation of the previous three breaths, dividing by three to obtain an average and dividing by two. The dose administered to the patient is directly proportional to the duration of the pulse of atomisation, and so the period of atomisation is summed, and the atomiser is switched off, or indicates that the patient should stop once the dose administered to the patient reaches the amount of medication prescribed for that treatment.

Other nebulisers are known in which the timed pulse of atomisation is other than 50% of the duration of inspiration. However, in these other nebulisers, the pulse length must be set for each patient by the clinician. Many of the nebulisers are, therefore, suitable only for use in a controlled environment, such as a hospital. The setting of the pulse length for each patient means that most nebulisers are not suitable for a patient to use at home.

Reference is made to International Patent Publication No. WO 97/48431, the contents of which are hereby incorporated by reference in its entirety. In addition, FIGS. 2 and 3 of this application show the nebuliser which is disclosed in the above International Patent application. Referring to FIG. 2, a mouthpiece 1 is shown through which a patient inhales in the direction of arrow 2. Below the mouthpiece 1 is a removable atomising section 3 which, in turn, rests on a base 4.

The base 4 is shown in more detail in FIG. 3. Referring to FIG. 3, the base 4 includes an inlet 5 through which air is supplied under pressure from a compressor (not shown). The pressurized air is led via a tube 6 to a manifold 7 which controls the flow of pressurized air to an air outlet 8 which directs air into the atomising section 3 shown in FIG. 2. The base 4 also includes a pressure sensor 9 which detects the pressure within the atomising section 3 via a port 10 electronic circuitry and a battery. The port 10 connects the pressure sensor 9 to the inside of the mouthpiece. This is attached to a printed circuit board 17 which is powered by the battery 19. When the pressure sensor detects that a patient has inhaled, the electronic circuitry controls the manifold 7 to divert pressurized air to the air outlet 8.

Referring again to FIG. 2, air under pressure passes through the air outlet 8 of the base 4 and is conducted through a tubular post 11 to an atomiser nozzle 12 out of which the air issues under pressure. A deflector 13 is located in the path of the pressurised air issuing from the nozzle 12 so that the pressurized air is deflected laterally so as to pass beneath a baffle 14. The passage of the pressurized air across the top of the tubular post 11 causes medication 15 to be drawn up between the outer surface of the tubular post 11 and the inner surface of a sleeve 16 which surrounds the tubular post 11. The medication 15 is atomised in the stream of air, and carried away in the stream of air below the rim of the baffle 14 and up through the mouthpiece 1 to a patient.

The pressure sensor 9 in the base 4 monitors the breathing pattern of a patient, and on the basis of the breathing pattern, the manifold 7 is controlled by the electronic circuitry to supply pressurized air to the atomising section 3 only during the first 50% of an inhalation phase incorporated in WO 97/48431.

BRIEF SUMMARY OF THE INVENTION

According to a first aspect of the present invention, a nebuliser comprises means for determination of the duration of a pulse of atomisation during inspiration, the determination means including means for measuring the tidal volume of a patient, timing means for measuring the duration of inspiration, means for storing an estimate of the volume of a patient's upper airway, and means for calculating the duration of the pulse on the basis of the tidal volume measured by the tidal volume measuring means, the duration of inspiration measured by the timing means, and the stored estimated volume of a patient's upper airway from the storage means.

According to a second aspect of the invention, a method for determining the duration of a pulse of atomization during inspiration during operation of a nebuliser comprises:

(i) measurement of the tidal volume of a patient;

(ii) measuring the duration of inspiration of a patient;

(iii) storing an estimate of the volume of a patient's upper airway; and (iv) calculating the duration of the pulse on the basis of the measured tidal volume of the patient, the measured duration of inspiration and the stored estimated volume of the patient's upper airway.

The means for calculating the duration of the pulse on the basis of the tidal volume is preferably comprised of a microprocessor, and the microprocessor might also be one of the elements of the tidal volume measuring means. The means for measuring the tidal volume of a patient includes a breathing sensor, which is preferably a peak flow sensor, but could be any one of a number of known sensors such as a pressure sensor. If a pressure sensor or the like is used, the microprocessor can determine to flow rate of each breath from the output of the sensor. From the sensor output it can determine the tidal volume. Associated with the microprocessor is an electronic memory in which data is stored, and in which is stored an estimate of the patient's upper airway, thereby constituting the means for storing an estimate of the patient's upper airway.

In this document, the upper airways of a patient are the mouth and trachea, and preferably include the volume of the nebuliser chamber.

The determination of the length of pulse of atomisation enables the proportion of the inhalation time during which atomisation occurs to be extended above 50% towards 100%. This will result in the patient receiving their treatment in a shorter time, since it will take fewer breaths to deliver the required dose of medication. However, there is no point in continuing atomisation into air which is inhaled by the patient at the end of his or her inspiratory phase (the 'end volume'), since it will remain in the upper airways. The medicine which does not go beyond the upper airways will be wasted when the patient exhales.

Thus, the invention according to the first and second aspects enables a pulse of atomisation to be generated which is longer than 50% but which stops atomisation before the end volume of inspiration begins. Another advantage of this invention is that a patient's adherence to the treatment regime will be much improved if the length of treatment is reduced.

In addition, the invention allows automatic optimisation of the pulse length without needing to be set by a clinician. This means that the pulse length will automatically be adapted to each patient on the basis of the patient's breathing pattern at the time the medication is being administered. Thus, the nebuliser may be used by the patient outside of the controlled environment of a hospital, and may be used at home. In addition, it is possible for the device to indicate when a dose has been administered without the patient needing to count the number of breaths which he or she has taken from the nebuliser.

According to the preferred embodiment, the means for measuring the tidal volume of a patient includes means for measuring a patient's peak flow, and tidal volume prediction means for calculating the tidal volume on the basis of the peak flow from the peak flow measuring means, and the duration of inspiration measured by the timing means. The means for measuring the patient's peak flow is a peak flow sensor or an airflow sensor such as a pressure sensor, the output of which is received by the processor. If the sensor is a pressure sensor or the like, the sensor identifies the peak pressure to determine the peak flow. The processor is the tidal volume prediction means.

Some or all of the values used in the calculations are mean values derived from a number of earlier measurements of each breathing pattern of the patient. For example, the patient will start inspiration through the nebuliser, and atomisation will not occur during the first three breaths. The first three breaths are analyzed by the nebuliser by recording the duration of inspiration, and the peak flows during inhalation as are required to determine the duration of a pulse of atomisation. Atomisation takes place on the fourth and subsequent breaths, in each case the values in the calculations are derived from a number of earlier measurements of the inspiration phase of a patient, in this case the previous three inspiratory phases.

Preferably, the atomisation is caused by a stream of gas under pressure passing through the nebuliser and sourced from a gas supply means. This gas is normally air, and the source is preferably a compressor operating together with an accumulator. During atomisation, gas from the accumulator is used to atomise the medication, and the compressor generates air under pressure to fill the accumulator. If a patient's inspiration is very long, the accumulator may be caused to be emptied, thereby disrupting atomisation. The atomiser, therefore, preferably includes a means for limiting the duration of the pulse so as to maintain the accumulator in a state where it is always under some pressure. In addition, the accumulator may include a valve which, when the accumulator is fall, vents gas to atmosphere thereby preventing it from becoming dangerously full. It is often preferable to maintain the compressor in operation all the time and to vent excess air to atmosphere rather than to switch the compressor on and off.

According to a third aspect of the present invention, a nebuliser comprises means no for predicting the tidal volume comprising means for measuring a patient's peak flow, timing means for measuring the duration of inspiration, and tidal volume prediction means for calculating the tidal volume on the basis of the peak flow from the peak flow measuring means, and the duration of inspiration measured by the timing means.

According to a fourth aspect of the invention, a method of predicting the tidal volume of a patient comprises:

(i) measuring a patient's peak flow;

(ii) measuring the duration of inspiration of a patient;

(iii) calculating the tidal volume on the basis of the measured peak flow, and the measured duration of inspiration of the patient.

Measuring the patient's respiratory volume (tidal volume) has previously involved continually monitoring the patient's inspiratory flow, typically every ten milliseconds. The flow rate is integrated over the duration of inspiration to determine the inspiratory volume. However, the third and fourth aspects of the invention determine the tidal volume of a patient much more simply. This invention reduces the amount of data processing which is required, thereby reducing the cost of the overall nebuliser. The peak flow is much simpler to measure, and can be used more simply in a calculation to determine the tidal volume.

BRIEF DESCRIPTION OF THE DRAWINGS

Embodiments of the present invention are described below by way of example, and with reference to the drawings in which.

DETAILED DESCRIPTION OF THE PREFERRED EMBODIMENTS

Figure 1:
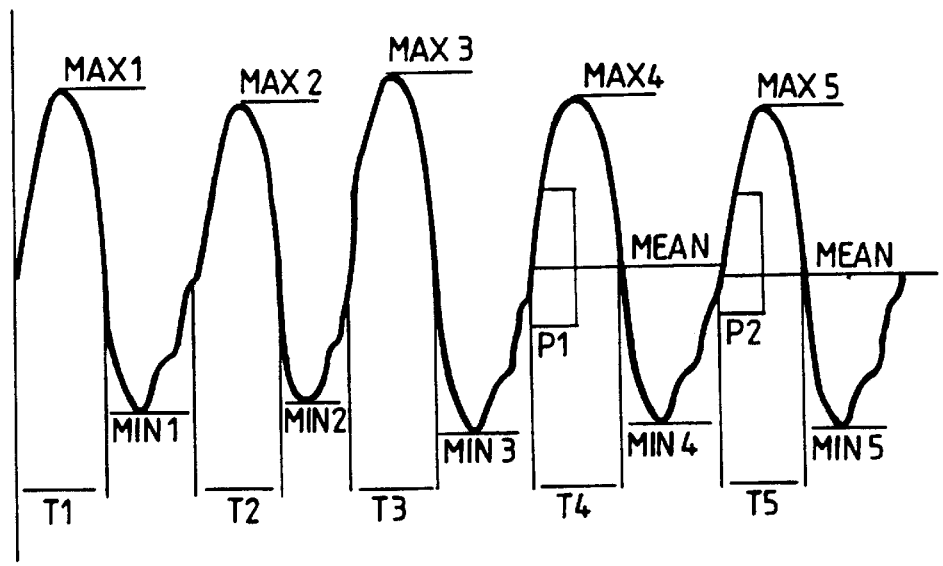
FIG. 1 is a graph showing the inhalation pattern of a patient over time, and indicating when the pulse of atomisation occurs in the first 50% of inspiration, as occurs in one known nebuliser.
Figure 2:
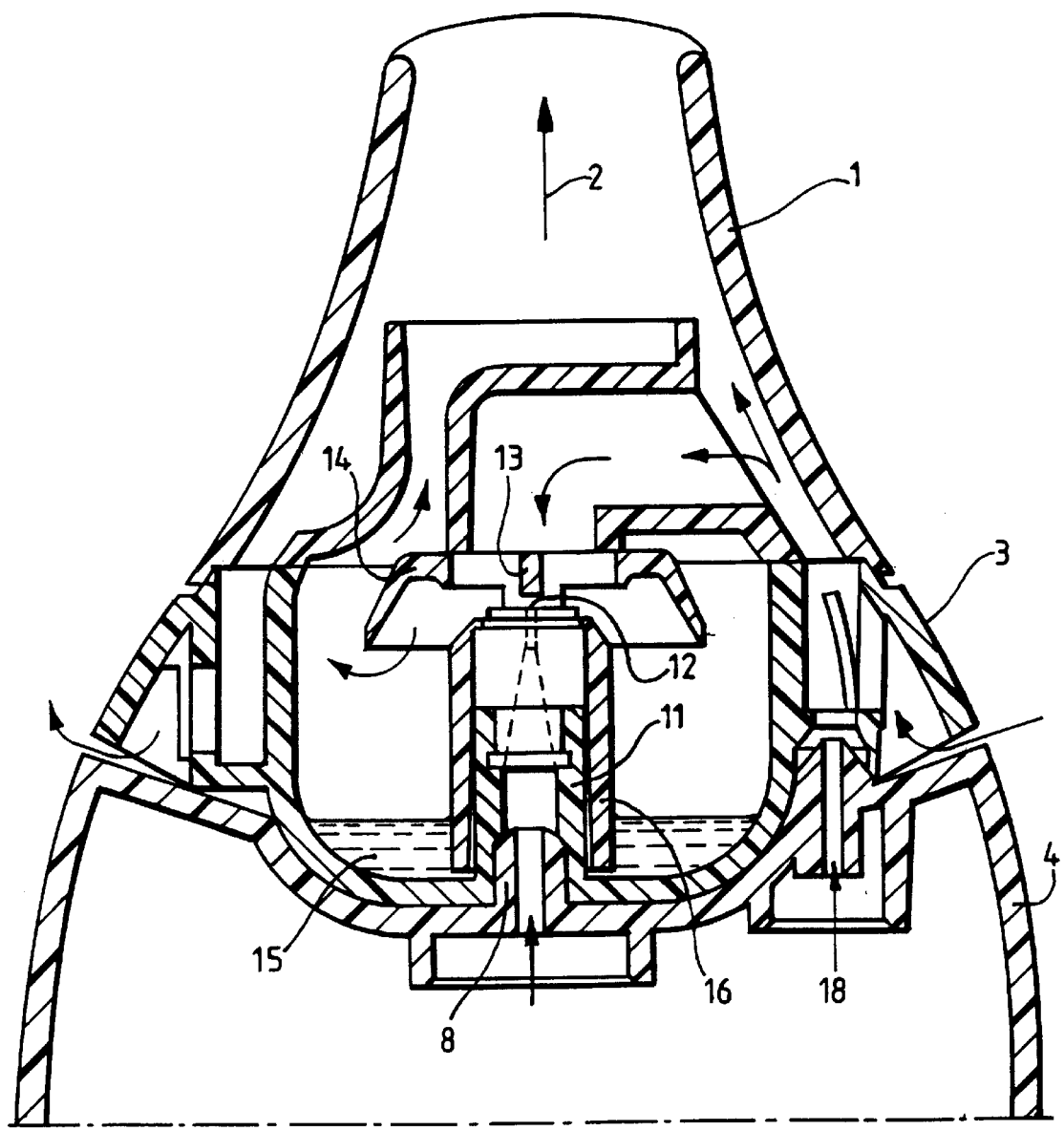
FIGS. 2 and 3 show a known nebuliser which generates pulses of atomisation during the first 50% of inspiration.
Figure 3:
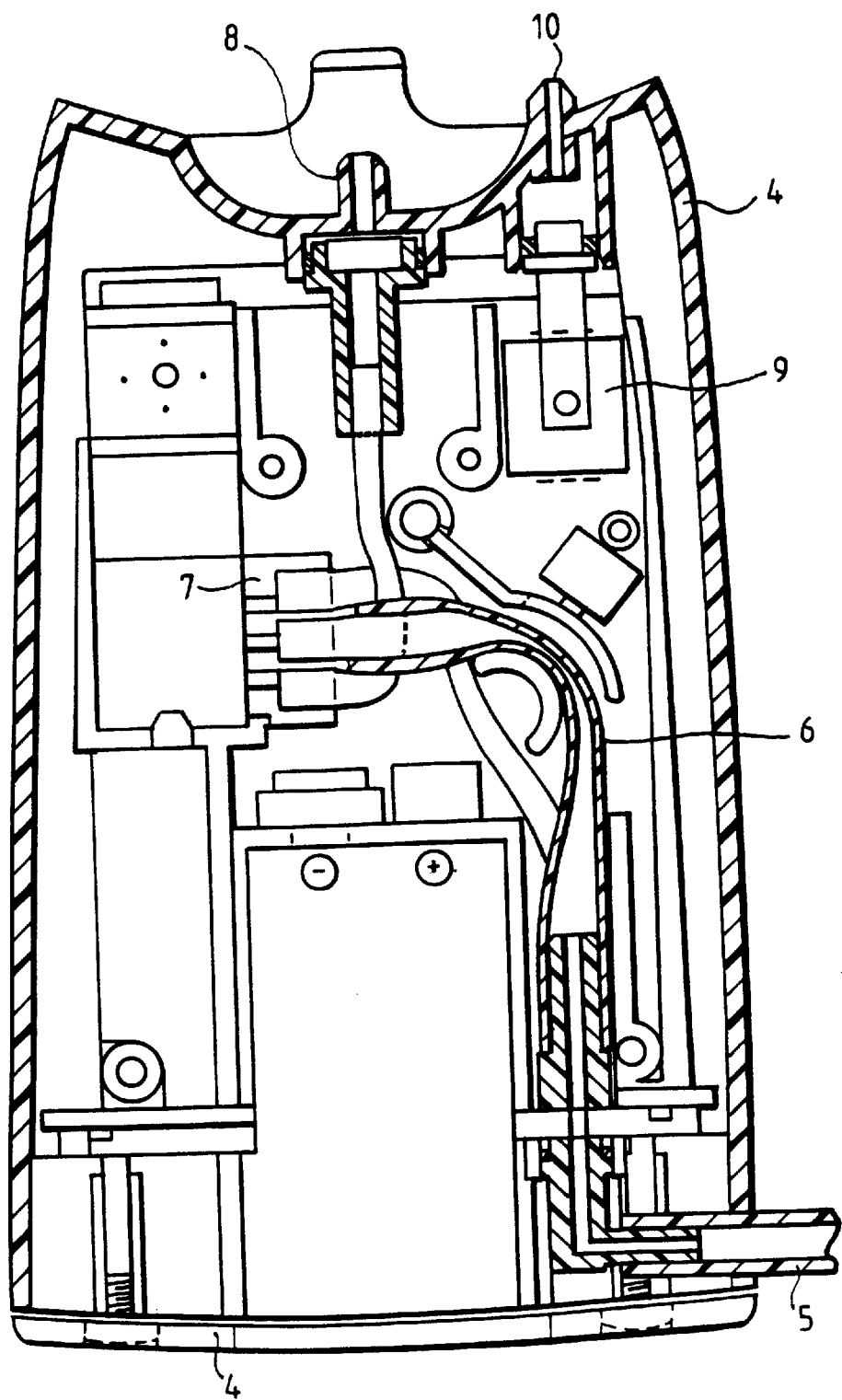

This invention applies to nebulisers of the type which generate pulses of atomisation, as in the prior art atomiser described above. The invention is not, however, limited to the exact atomiser described above, but may be applied to other nebulisers. For convenience, the description below of the present invention will refer to components of the prior art device shown in FIGS. 2 and 3, and because many of the components, for example, the manifold, may be used in the present invention. The preferred nebuliser comprises one of a jet nebuliser, ultrasonic nebuliser or a pressure mesh nebuliser.

Jet nebulisers are of two kinds, these being air-jet nebulisers and liquid-jet nebulisers. An example of an air-jet nebuliser, which uses a source of compressed air to nebulise a liquid, is disclosed in EP 0627266 (Medic-Aid Limited), the content of which is incorporated herein by reference. An example of a liquid-jet nebuliser, which drives a liquid through one or more nozzle outlets to produce a spray of fine droplets is disclosed in WO 94/07607 (Boehringer Ingelheim International GmbH et al), the content of which is incorporated herein by reference.

Ultrasonic nebulisers which nebulise a liquid using ultrasonic waves usually developed with an oscillating piezo-electric element, take many forms, these including nebulisers where liquid is in direct contact with the piezo-electric element, where there is an amplifying interface, typically an enclosed fluid, between the piezo-electric element and the liquid, and where the piezo-electric element vibrates a mesh from which an aerosol is generated. Examples of ultrasonic nebulisers are disclosed in U.S. Pat. No. 4,533,082 (Maehara et al) and U.S. Pat. No. 5,261,601 (Ross et al), the contents of which are incorporated herein by reference. The nebulisers described in those documents include a housing that has a reservoir which holds a quantity of liquid to be dispensed, which housing has a perforated membrane in contact with the reservoir and an ultrasonic vibrator connected to the housing to vibrate the perforated membrane. Another example of an ultrasonic nebuliser is described in WO 97/29851 (Fluid Propulsion Technologies, Inc), the content of which is incorporated herein by reference. An example of a pressure mesh nebuliser, which may or may not include a piezo-electric element, is disclosed in WO 96/13292 (Aradigm Corporation), the content of which is incorporated herein by reference.

In WO 96/13292, aerosolized bursts of a formulation of a respiratory drug are disclosed for delivery into a patient's inspiratory flow. Release automatically occurs each time at the same point in the patient's inspiratory flow. The release point is preferably calculated by a microprocessor which receives data from a sensor making it possible to determine inspiratory flow rate and inspiratory volume. The microprocessor is included in combination with a read/write non-volatile memory means which is readable by an external device. The microprocessor will also include a timing device. The microprocessor calculates the dose given to the patient so that the progression of treatment can be displayed to the patient.

Extending the proportion of the inhalation of the patient in which atomisation takes place above 50% results in the patient receiving their treatment faster since it will take fewer breaths to deliver the required volume of medication. However, to avoid wastage of the medication which is atomised in the end volume of patient's inspiratory volume, the pulse of atomisation must be stopped before the end volume is reached. The end volume is the volume of air inhaled by a patient at the end of the inspiratory volume which remains in the upper airways (the mouth and trachea) and does not enter into the lower parts of the lungs. Medication which is atomised into the end volume is wasted when the patient exhales, together with any air atomised medication left in the nebuliser, since it does not reach the lungs.

The end volume is the volume of the patient's upper airway, and is proportional to the size of the patient. Clearly, the end volume will vary as a percentage of the inspiratory tidal volume since the tidal volume changes significantly depending on the type and extent of the respiratory disease suffered by the patient. The optimum duration of atomisation pulse would, therefore, be from the start of inhalation up to the point during inspiration when the volume remaining to be inspired equals the end volume. Atomisation would then be stopped and the remaining end volume would clear the atomised medication from the device and the upper airways of the patient and into the lungs. Thus, the percentage of inspiration in which atomised medication is delivered is maximised, thereby minimising treatment time and still avoiding wastage of medication. The length of the atomnisation pulse calculated by the processor is dependent upon the patient's inspiratory tidal volume. The nebuliser must therefore measure the patient's tidal volume, preferably on a breath by breath basis so that the processor is able to calculate, for example from the previous three breaths, an average inhalation volume for the next breath. Thus, the atomisation pulse time will be calculated by the processor as follows:

Pulse time=mean inspiratory time×(mean tidal volume−end volume)/mean tidal volume Timing means are included in the nebuliser connected to the pressure sensor 9 (shown in FIG. 3) in order to measure the duration of inspiration. Storage means are also included in the nebuliser in which an estimate of the end volume of a particular patient is stored. Since this figure is a constant value for a particular patient, this can be entered at the beginning of a course of treatment, and is estimated on the basis of the size of the patient. The storage means for storing an estimate of the end volume is an electronic memory associated with the microprocessor, and into which the estimate is stored prior to use of the nebuliser. The estimate is used by the microprocessor during calculations. The nebuliser includes a means for measuring the tidal volume of a patient. According to one form of the invention, the patient's inspiratory flow is monitored continuously, typically every ten milliseconds, and this is integrated over the inspiratory duration. Another, simpler, way of measuring the tidal volume of a patient is described later in this specification.

The nebuliser also includes means for calculating the atomisation pulse time on the basis of the duration of inspiration, the tidal volume and the end volume. The calculation means carries out the calculation outlined above.

In view of the fact that the nebuliser adapts to the breathing pattern of a patient, when the patient starts breathing, no atomisation takes place during the first three breaths. Those first three breaths are used to analyse the breathing pattern of the patient. The flow rate of the first three breaths are measured, and from this, the duration of the inhalation phase of the first three breaths are calculated, and an average found. The average duration of inhalation is then used in the calculation to determine the pulse length of atomisation during the fourth breath. In addition, as the patient continues to breathe in and out, the previous three breathing patterns are measured and used to calculate the next pulse duration. Thus, if a patient's breathing pattern improves during treatment, the nebuliser will adapt to this change in order to optimise the dose administered during each breath.

Figure 4:
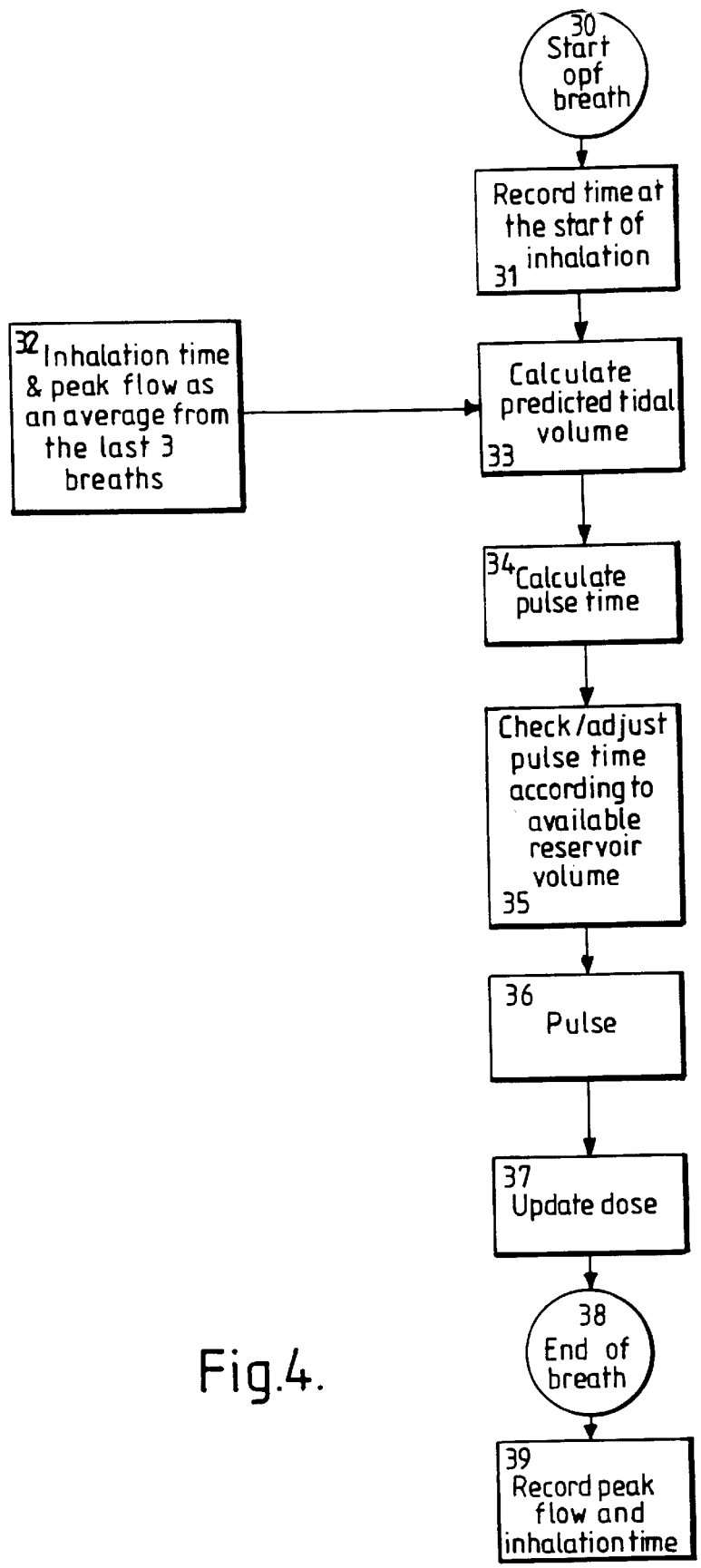
FIG. 4 is a flow diagram showing how the pulse of atomisation during inspiration is determined.

Referring now to FIG. 4, the steps taken by the nebuliser, and by the patient are described. The first operation, box 30 represents the patient starting to inhale. The timing means records the time at which inhalation starts as shown in box 31, and during inhalation, a calculation is performed to predict the tidal volume of the patient as shown in box 33. This step will be described in more detail later in the specification, but it will be noted that the calculation requires data to be included in the calculation which is the inhalation time and peak flow as an average from the last three breaths, as shown in box 32. The pulse time is then calculated by the calculation means as shown in box 34, and the pulse time is adjusted, as shown in box 35 in the event that the pulse length would exhaust an accumulator from which is pressurised air is supplied to the nebuliser. This step, shown in box 35 is also described in more detail later in this specification. The pulse of atomisation occurs during inhalation, and after it has stopped, a calculation is carried out to determine what dose has been atomised. At the end of the breath as shown in box 38, details of the peak flow of the patient inhalation, and the duration of inhalation are recorded so that calculations determining pulse length may be made for subsequent breaths. This is shown in box 39.

Reference is made above to the simpler prediction of tidal volume. As will be appreciated, measuring tidal volume by integrating measured flow rate over the time of inspiration requires considerable processing power and is relatively expensive. A simpler method of determining the tidal volume is proposed which requires much simpler calculations and much simpler measurements to be made for use in such a calculation. To carry out the measurement, the nebuliser includes a peak flow detector for detecting the peak flow rate of inspiration.

The calculated, or predicted tidal volume is derived from the peak flow measured by the peak flow detector, and the duration of inspiration measured by the timer. The tidal volume implemented by the processor carries out the following calculation:

$$\text{Predicted tidal volume} = C \times \text{Mean Peak Flow} \times \frac{\text{Inspiratory Time}}{60}$$

$C$ is a constant and it is found that $C = 0.7$

Figure 5:
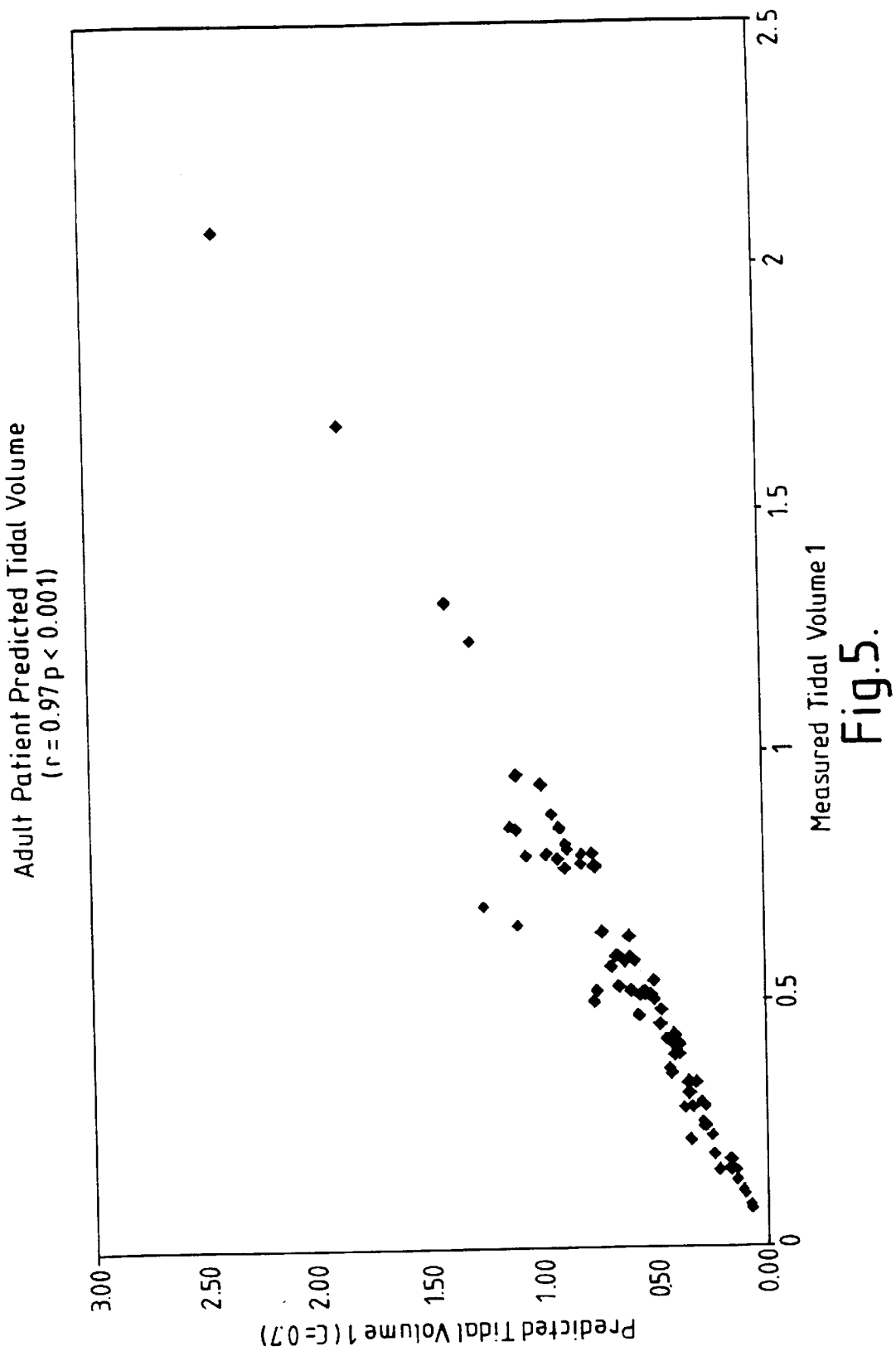
FIG. 5 is a graph showing the predicted tidal volume against measured tidal volume.

FIG. 5 is a graph of the predicted tidal volume against measured tidal volume. Each point on the graph represents a patient whose tidal volume has been measured by a complex tidal volume calculation by integration of the patient's inspiratory flow over the duration of inhalation, and the predicted tidal volume according to the new, simpler method of calculation. It will be seen that the predicted tidal volumes are extremely accurate, and so the predicted tidal volume may be included in the calculation of atomisation pulse time.

The use of a low flow rate compressor together with a accumulator to supply compressed air to the nebuliser is disclosed in our earlier Patent application published as WO 97/48431, which is referred to above. In the past, the size of the compressor and accumulator are selected so that the maximum pulse that can be delivered by the device (currently 50% of inspiratory time) does not exceed the accumulator volume for any given pulse or the mean output of the compressor. Now that the pulse time is variable, it is preferable to calculate the maximum pulse time available from the air supply system. For patients who have a slightly higher inspiratory demand, the pulse time of atomisation will be reduced so that the supply capability of the air supply system is not exceeded. The calculations are carried out on a breath by breath basis, assuming that the accumulator is filled at constant flow rate from the compressor. The volume of air added to the accumulator from the end of previous pulse to the start of the next pulse is calculated and then added to the volume remaining at the end of the previous pulse.

Figure 6:
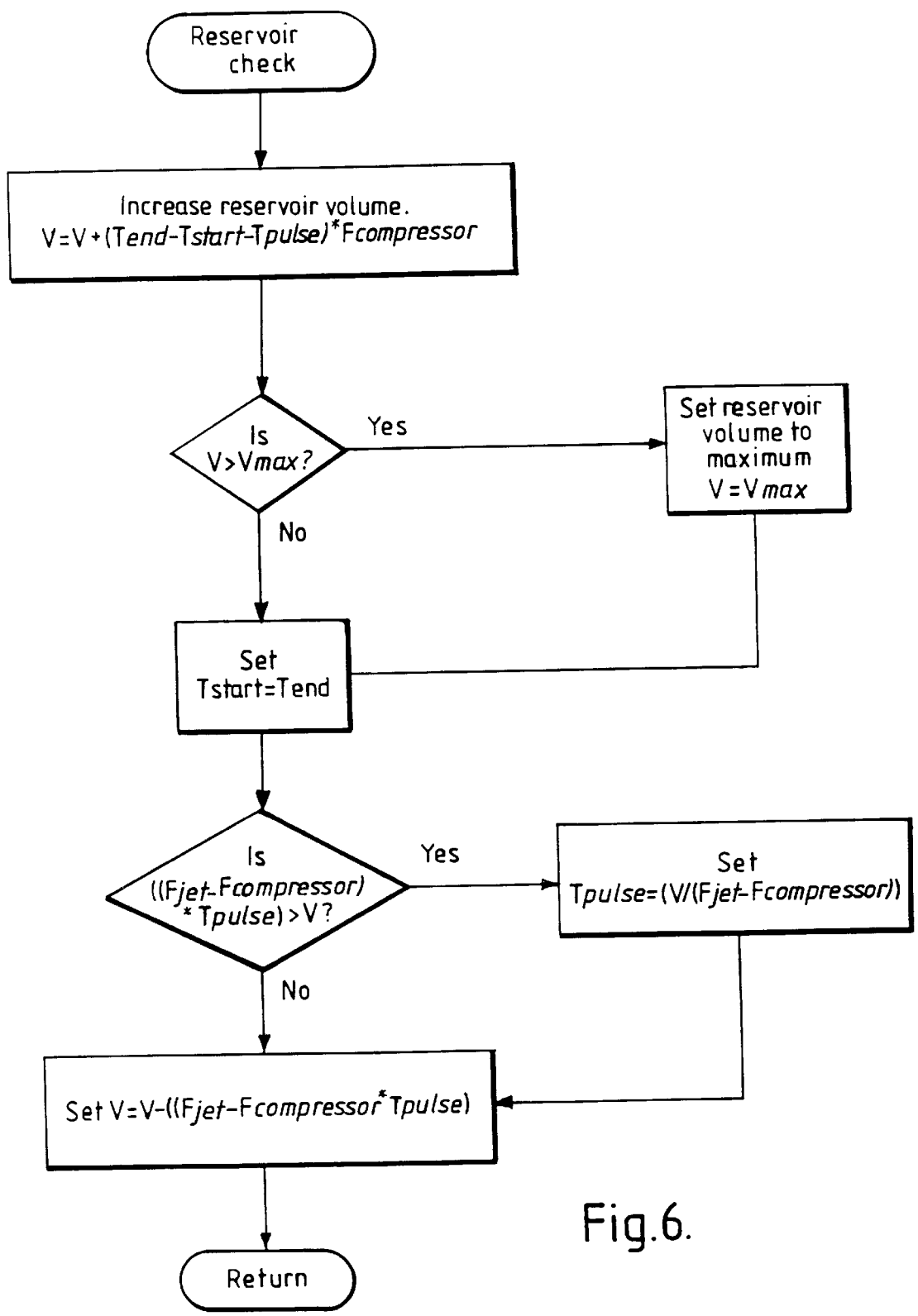
FIG. 6 is a flow diagram showing the limitation of the pulse length depending on the supply of pressurised gas.

FIG. 6 is a flow diagram showing the calculations carried out in ensuring that the volume of air used does not exceed the volume of the accumulator. If the air in the accumulator is calculated to be above the maximum volume of the accumulator, the volume is set to be at its maximum $V=V_{max}$. This is because there is an automatic vent valve which limits the volume of air stored in the accumulator. The maximum pulse time can then be calculated on the basis of the rate of flow of air out of the accumulator which is the flow to the atomiser jet, minus the flow rate to the compressor. If this exceeds the volume available in the accumulator, then the pulse time is limited to the current accumulator volume. The volume of accumulator at the end of the pulse is then calculated to be used at the beginning of the next calculation occurring at the beginning of the next inhalation of the patient. Thus, the maximum pulse time for individual breaths is calculated without exceeding the capacity of the air supply system. The compressor has a constant output flow rate, typically 1.5 litres per minute and the nebuliser jet has a flow rate of 6 litres per minute during pulsing. The accumulator has a volume of approximately 150 millilitres at NTP.

Figure 7:
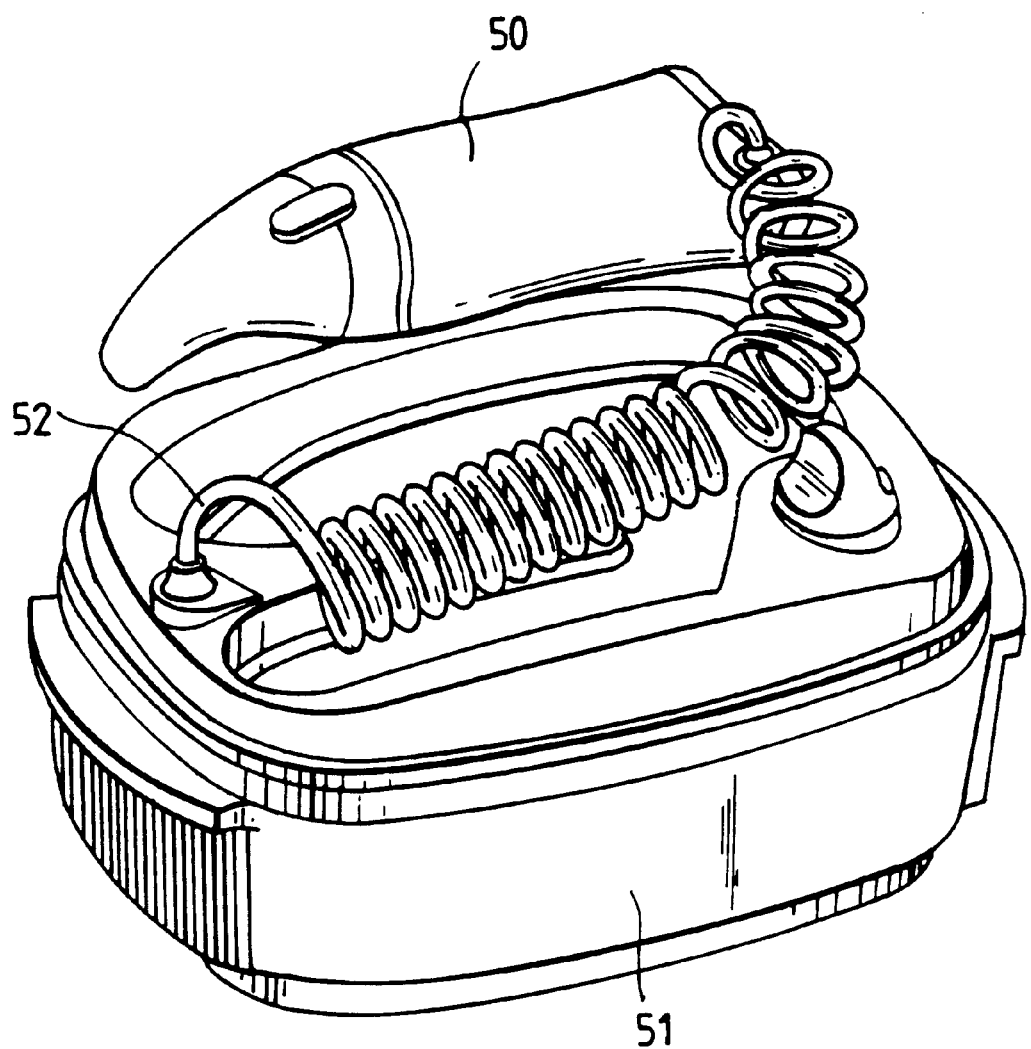
FIG. 7 shows the nebuliser together with a source of pressurised gas.

FIG. 7 shows the nebuliser 50 connected to the air supply 51 by a flexible tube 52.

Figure 8:
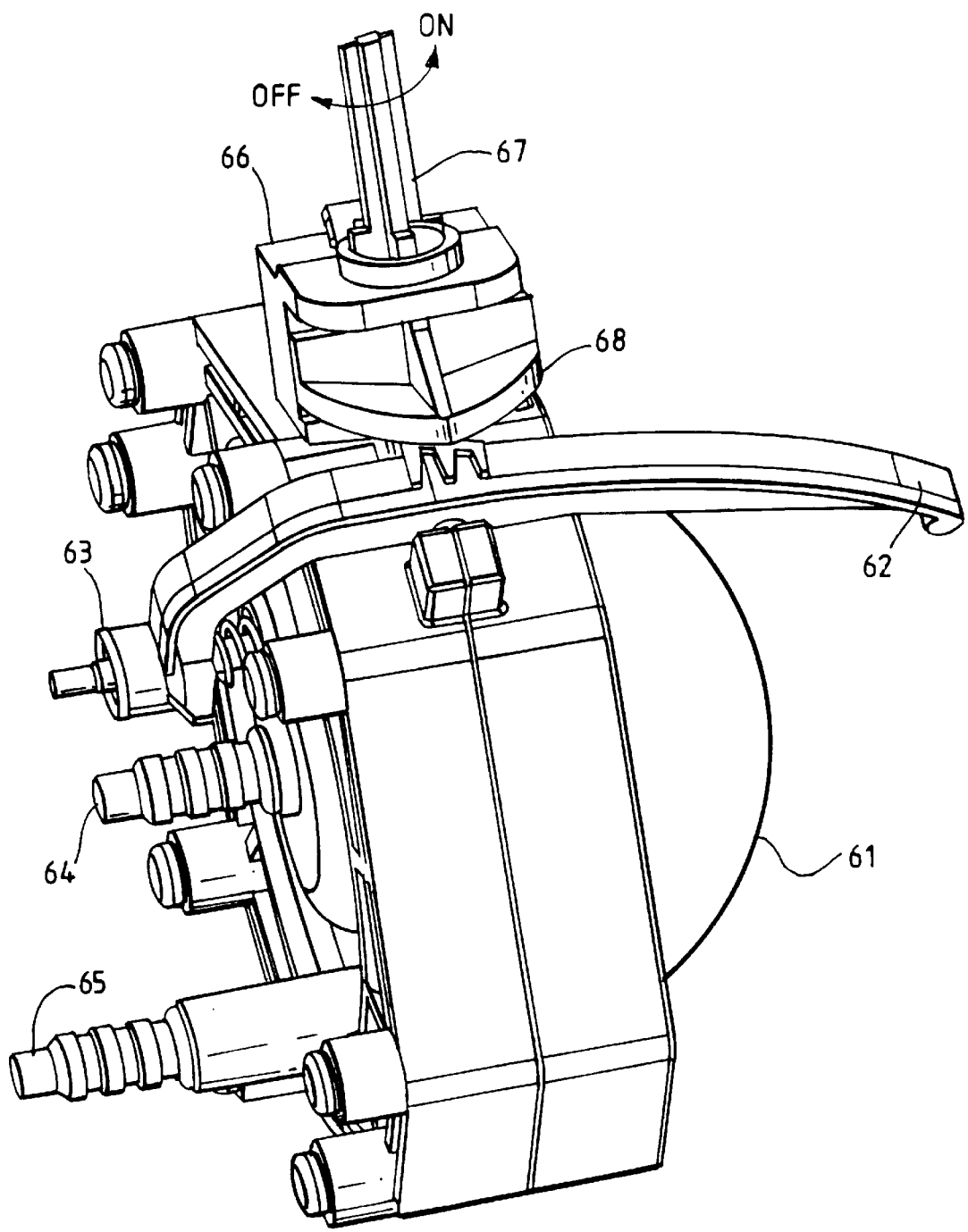
FIG. 8 shows an air accumulator within the air supply.

Referring to FIG. 8, the accumulator is shown which has a vent 63, thereby limiting the maximum expansion of the accumulator. As each pulse is delivered to the nebuliser, the diameter of the accumulator is reduced, and the vent 63 is closed.

The compressor may be mains powered or battery powered. The pump, especially a mains powered pump, operates continually during use, and operates to inflate the accumulator. When the pressure in the accumulator reaches the required level, a pressure switch in the hand-held part of the nebuliser is activated as is described in an earlier Patent application referred above. That switches the nebuliser ON. Once the treatment has been completed, the compressor is switched OFF. The accumulator deflates and the pressure switch in the hand-held part of the nebuliser deactivates the unit.

Referring to FIG. 8, the pump supplies air to the accumulator via a port 64. Inflation of the diaphragm 61 of the accumulator is controlled by an assembly including an arm 62 which is connected to a vent valve 63. When the diaphragm 61 of the accumulator reaches the maximum desired extension, it contacts the arm 62 to open the vent valve 63. This releases to atmosphere the flow of air from the compressor, and maintains the accumulator at a fixed extension. During use, air is removed from the accumulator via port 65 and the diaphragm 61 shrinks and loses contact with the vent arm 62 which closes the valve 63 allowing the compressor to recharge the accumulator until the vent arm 62 again operates the vent valve 63.

It is also advantageous to vent the accumulator to atmosphere when the compressor is switched off, and this is achieved by mounting the main power switch 66 on top of the accumulator with a rotary knob 67. The bottom of the knob 67 includes a cam 68 which contacts the vent arm 62 to open the vent 63 thereby releasing pressure from the accumulator. Simultaneously, the compressor is switched off. When the compressor is switched back on again, the cam 68 is disengaged from the vent arm 62, thereby closing the vent valve 63.

Figure 9:
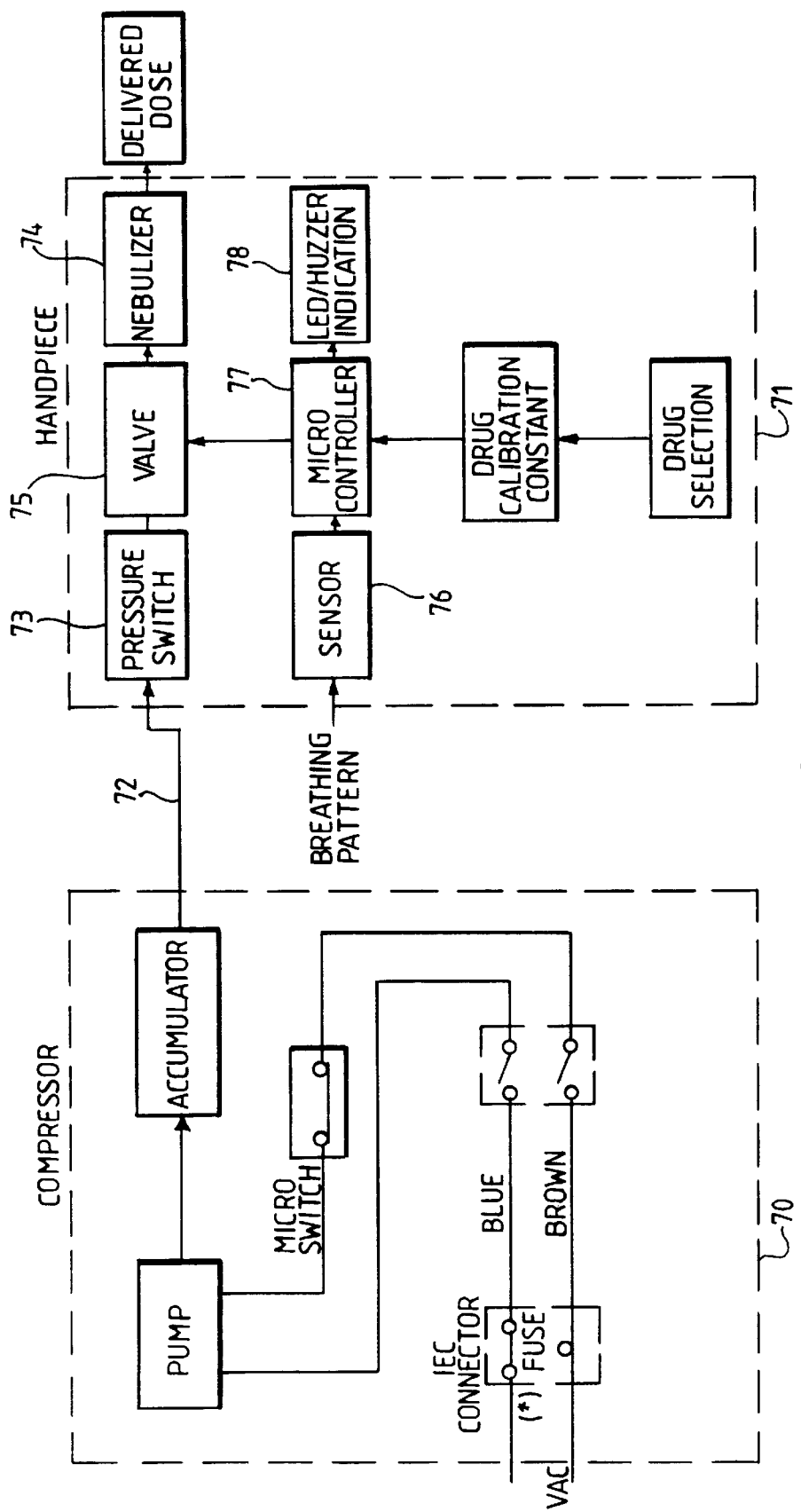
FIG. 9 is a schematic drawing showing the way in which the nebuliser is controlled.

Finally, FIG. 9 illustrates a simplified form of the way in which all of the components of nebuliser are connected together. The compressor and accumulator 70 are shown as being separate from the hand-held part of the nebuliser 71, but connected by a tube 72 carrying the pressurised air into the nebuliser 71. In the compressor and accumulator part 70, the pump is shown to supply the accumulator 70 with compressed air. In the nebuliser part 71, the nebuliser is switched on at the pressure switch 73 by the presence of pressurised air in tube 72. The nebulising part 74 of the nebuliser is controlled by a valve or manifold 75 which controls the pulses of pressurised air. The breathing pattern of a patient is detected by a sensor 76 which delivers information regarding the breathing pattern to the microcontroller 77 which, in turn, controls the manifold 75. Once a dose of medication has been delivered, indication means, such as a LED or buzzer 78 is activated by the microcontroller to indicate to the patient that treatment is complete.

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents, and other publications cited herein are incorporated by reference in their entirety.

What is claimed is:

1. A nebuliser comprising means for determining the duration of a pulse of atomisation during inspiration, the determination means including:
   (i) means for measuring the tidal volume of a patient,
   (ii) timing means for measuring the duration of inspiration,
   (iii) means for storing an estimate of the volume of a patient's upper airway, and
   (iv) means for calculating the duration of the pulse on the basis of the tidal volume measured by the tidal volume measuring means, the duration of inspiration measured by the timing means, and the stored estimated volume of a patient's upper airway from the storage means.

2. A nebuliser according to claim 1, wherein the means for measuring the tidal volume of a patient includes means for measuring a patient's peak flow, and tidal volume prediction means for calculating the tidal volume on the basis of the peak flow measured by the peak flow measuring means, and the duration of inspiration measured by the timing means.

3. A nebuliser according to claim 1, wherein some or all of the values used in the calculations are mean values derived from a number of earlier measurements of the breathing pattern of the patient.

4. A nebuliser according to claim 1, farther comprising a source of pressurised gas for atomising the medication, the source including an accumulator for accumulating the gas, and means for limiting the duration of the pulse so as to maintain the accumulator in a state where it is always under some pressure.

5. A nebuliser according to claim 4, wherein the accumulator includes a valve which, when the accumulator is fall, vents gas to atmosphere.

6. A method for determining the duration of a pulse of atomization during inspiration, comprising:
   (i) measurement of the tidal volume of a patient;
   (ii) measuring the duration of inspiration of a patient;
   (iii) storing an estimate of the volume of a patient's upper airway; and
   (iv) calculation of the duration of the pulse on the basis of the measured tidal volume of the patient, the measured duration of inspiration and the stored estimated volume of the patient's upper airway.

7. A method according to claim 6, wherein the measurement of the tidal volume of a patient comprises:
   (v) measuring the peak flow of a patient; and
   (vi) predicting the patient's tidal volume on the basis of the measured peak flow, and the measured duration of inspiration.

8. A method according to claim 6, wherein calculations are carried out on mean values derived from a number of earlier measurements of the breathing pattern of the patient.

9. A nebuliser comprising means for predicting the tidal volume including means for measuring a patient's peak flow, timing means for measuring the duration of inspiration, and tidal volume prediction means for calculating the tidal volume on the basis of the peak flow from the peak flow measuring means, and the duration of inspiration measured by the timing means.

10. A nebuliser according to claim 9, wherein some or all of the values used in the calculations are mean values derived from a number of earlier measurements of the breathing pattern of the patient.

11. A method of predicting the tidal volume of a patient comprising:
    (i) measuring a patient's peak flow;
    (ii) measuring the duration of inspiration of a patient;
    (iii) calculating the tidal volume on the basis of the measured peak flow, and the measured duration of inspiration of the patient.

12. A method according to claim 11, wherein calculations are carried out on mean values derived from a number of earlier measurements of the breathing pattern of the patient.

13. A nebuliser comprising:
    means for atomising a medication;
    means for monitoring a patient's breathing pattern; and
    means for controlling the atomising means to atomise the medication in pulses,
    wherein the length of the pulses, and their proportion of the inspiratory phase of the breathing pattern are varied by the controlling means depending on the breathing pattern monitored by the monitoring means.

* * * * *